United States Patent
Riva et al.

(10) Patent No.: US 11,174,498 B2
(45) Date of Patent: Nov. 16, 2021

(54) PROCESS FOR PRODUCING A BIO-PRODUCT

(71) Applicant: Versalis S.p.A., San Donato Milanese (IT)

(72) Inventors: Daniele Riva, Prelà (IT); Dario Giordano, Tortona (IT)

(73) Assignee: Versalis S.p.A, San Donato Milanese (IT)

( * ) Notice: Subject to any disclaimer, the term of this patent is extended or adjusted under 35 U.S.C. 154(b) by 0 days.

(21) Appl. No.: 16/095,996

(22) PCT Filed: May 2, 2017

(86) PCT No.: PCT/EP2017/060336
§ 371 (c)(1),
(2) Date: Oct. 24, 2018

(87) PCT Pub. No.: WO2017/191091
PCT Pub. Date: Nov. 9, 2017

(65) Prior Publication Data
US 2019/0136279 A1      May 9, 2019

(30) Foreign Application Priority Data
May 3, 2016  (EP) ..................... 16425038

(51) Int. Cl.
| | |
|---|---|
| *C12P 19/04* | (2006.01) |
| *C13K 1/02* | (2006.01) |
| *D21C 1/02* | (2006.01) |
| *D21C 11/00* | (2006.01) |
| *C12P 7/10* | (2006.01) |
| *D21C 5/00* | (2006.01) |
| *C12P 19/02* | (2006.01) |
| *C13K 13/00* | (2006.01) |

(52) U.S. Cl.
CPC .................. *C12P 19/04* (2013.01); *C12P 7/10* (2013.01); *C12P 19/02* (2013.01); *C13K 1/02* (2013.01); *C13K 13/00* (2013.01); *C13K 13/002* (2013.01); *D21C 1/02* (2013.01); *D21C 5/00* (2013.01); *D21C 11/0007* (2013.01); *C12P 2201/00* (2013.01); *Y02E 50/10* (2013.01)

(58) Field of Classification Search
None
See application file for complete search history.

(56) References Cited

U.S. PATENT DOCUMENTS

| 2,516,833 A | 8/1950 | Viljo |
| 2009/0221814 A1 | 9/2009 | Pschorn et al. |

FOREIGN PATENT DOCUMENTS

| EP | 0035679 A1 | | 9/1981 |
| WO | 2009/108773 A2 | | 9/2009 |
| WO | WO 2009/108773 | * | 9/2009 |
| WO | 2010/113129 A2 | | 10/2010 |
| WO | WO 2010/113129 | * | 10/2020 |

OTHER PUBLICATIONS

Fu Xiaoguo et al., "Air-steam explosion enhancing the extraction efficiency of chlorogenic acid from leaves of Eucomia ulmoides01", Separation and Purification Technology, Apr. 3, 2015, pp. 317 to 325, vol. 146.

* cited by examiner

*Primary Examiner* — Erin M. Bowers
(74) *Attorney, Agent, or Firm* — Edwin A. Sisson, Attorney at Law, LLC; Jeffrey J. Banyas

(57) ABSTRACT

It is disclosed a process for producing a bio-product from a ligno-cellulosic biomass, wherein the ligno-cellulosic biomass, a gas and steam are introduced in a pressurized reactor operated in a continuous manner at conditions to have a vapor head space. In the pressurized reactor, the vapor head space is maintained at a vapor head space temperature and at a pressure which is at least 1 bar greater than a pure steam equilibrium pressure at the vapor head space temperature. The ligno-cellulosic biomass is then refined by rapidly releasing the pressure while discharging the ligno-cellulosic biomass from the pressurized reactor assembly to create a pre-treated ligno-cellulosic biomass, which is then hydrolyzed and converted to the bio-product. Preferably, at least a portion of the gas is air entrapped in the ligno-cellulosic biomass and it is introduced into the pressurized reactor as part of the ligno-cellulosic biomass. In a preferred embodiment, the lignocellulosic biomass is subjected to a soaking step and an aeration step prior to being introduced into the pressurized reactor, without any xylans separation step.

19 Claims, No Drawings

PROCESS FOR PRODUCING A BIO-PRODUCT

PRIORITIES AND CROSS REFERENCES

This application claims priority from International Application No. PCT/EP2017/060336 filed on 2 May 2017 which claims priority from European Application No. 16425038.3 filed on 3 May 2016, the teachings of each of which are incorporated by reference herein in their entirety.

BACKGROUND

Bio-chemicals and bio-fuels made using second generation processes ferment glucose, a C6 simple sugar derived from cellulose (glucans) of a ligno-cellulosic biomass as opposed to the first generation processes which ferment glucose derived from starch.

It is well known that the C6 sugars in ligno-cellulosic biomasses are not readily accessible to enzymes and need a pre-treatment in order to increase the accessibility of the glucans to the enzyme hydrolysis. Typically, this pre-treatment involves a steam explosion to open the cells of the ligno-cellulosic biomass and make the glucans more accessible to subsequent enzyme hydrolysis and fermentation steps.

It is also well known that ligno-cellulosic biomasses contain hemi-cellulose or xylans (C5 sugars) and that the xylans of the hemicellulose degrade at the temperatures used for the steam explosion of the ligno-cellulosic biomass.

WO 2009/108773 titled SYSTEM AND METHOD FOR PRE-EXTRACTION OF HEMICELLULOSE THROUGH USING A CONTINUOUS PREHYDROLYSIS AND STEAM EXPLOSION PRETREATMENT PROCESS, teaches this conventional wisdom stating that "[h]igh pressures and/or high temperatures are typical in pre-treatments used to generate alcohols, e.g. ethanol, from cellulosic feed-stocks. In these conventional pre-treatments, some C5 sugars are converted to components which inhibit the alcohol fermentation of C6 sugars in the fermentation step following pre-treatment. Removing these inhibiting components, such as aldehydes (e.g. HMF, furfural, and formaldehyde), monomeric phenolics (e.g., vanillin and coniferyaldehyde), acids, (e.g., formic acid) and other inhibitors should increase the alcohol yield in the C6 fermentation step following pre-treatment."

Separating the C5 sugars from the ligno-cellulosic biomass is not new. For example, U.S. Pat. No. 2,516,833 published Aug. 1, 1950 teaches hydrolyzing the ligno-cellulosic biomass at a low temperature to recover the pentoses (C5 sugars) followed by processing at a higher temperature to recover the hexoses (C6 sugars). The industry has continued with this approach to this day.

The solution advocated by WO 2009/108773 utilizes the well-known two stage process where the ligno-cellulosic biomass is cooked under mild conditions to hydrolyze and dissolve hemi-cellulose from the feedstock. The hemi-cellulose is dissolved into a liquid to extract C5-sugars before the feed stock flows to a second pressurized reactor to cook the remaining cellulose in the feed stock. WO 2009/108773 notes that after "[h]aving been separated from the feed stock in the tank, the C5-sugars in the hemi-cellulose may be converted by conventional processes to Xylose for use as food additives, biogas by aerobic and anaerobe fermentation, methyl-furan by high octane oxygenate, and to an aqueous sugar for conversion to alcohols, such as ethanol."

This conventional two stage process represents the current state of the art of ligno-cellulosic biomass processing. WO 2010/113129 discloses data supporting the benefit of removing the hemi-cellulose prior to steam explosion. For example, Arundo Donax was subjected to steam explosion with and without removing the hemi-cellulose. When the hemi-cellulose is removed, only 1.3% of the xylans present in the raw material are degraded to inhibitor compounds (Example 5) with the pretreatment, while in the steam explosion process without removing the hemi-cellulose, 19.3% (Example 1) and 63.8% (Example 2) of the xylans are degraded to inhibitor compounds.

In fact, Bertil Stromberg, an inventor of WO 2009/108773 supports the industry understanding that it is technically impossible to simultaneously process C5s and C6s without producing significant inhibitors in his declaration to the United States Patent Office in 2016. In that declaration he states that "[a]s discussed in the 512 Patent [the U.S. patent claiming priority from WO 2009/108773], hemi-cellulose (which is mainly 5-carbon sugars, also referred to in the 512 patent as "C5 sugars") is dissolved and hydrolyzed by the hydrolysis reaction in the first pressurized reactor. The C5 sugars generated in the first pressurized reactor are removed by washing and draining the feed stock. If not washed and drained out of the feed stock, the C5 sugars would remain in the feed stock and degrade in the second reactor and form potential inhibitors to the subsequent enzymatic hydrolysis and/or fermentation steps."

As is readily apparent, the two stage processes require at least two separate reactors, separate handling and recovery systems and are much more complicated in design and more capital intensive than a single reactor.

There exists therefore, the need for a pre-treatment process which provides both a high glucans accessibility and high xylans recovery (i.e. little xylan degradation) without separating the xylans from the ligno-cellulosic biomass and thus avoiding the complex designs and schemes of 66 years of prior art proposals and conventional wisdom.

SUMMARY

It is disclosed a process for producing a bio-product from a ligno-cellulosic biomass comprised of a total amount of xylans, a total amount of glucans, a total amount of lignin, and water. The process comprises the steps of: introducing the ligno-cellulosic biomass, a total amount of gas, and steam into a pressurized reactor of a pressurized reactor assembly operated in a continuous manner at conditions to have a vapor head space in the pressurized reactor, wherein a portion of the steam condenses on the ligno-cellulosic biomass with the pressurized reactor; maintaining the ligno-cellulosic biomass in the pressurized reactor at a ligno-cellulosic biomass pressure greater than 10 bar for a residence time from 0.5 minutes to 120 minutes, at a vapor head space temperature in a range of 130° C. to 230° C., wherein the ligno-cellulosic biomass pressure is at least 1 bar greater than a pure steam equilibrium pressure at the vapor head space temperature; refining the ligno-cellulosic biomass by rapidly releasing the ligno-cellulosic biomass pressure while discharging the ligno-cellulosic biomass from the pressurized reactor assembly to create a pre-treated ligno-cellulosic biomass; hydrolyzing at least a portion of the glucans to an amount of glucose; and converting at least a portion of the amount of glucose to the bio-product.

It is also disclosed that the ligno-cellulosic biomass may further comprise an entrapped air, and that at least a portion of the gas may be the entrapped air introduced into the pressurized reactor as part of the ligno-cellulosic biomass.

It is further disclosed that the process may further comprise a xylans separation step, wherein less than 15% of the total amount of xylans are separated from the ligno-cellulosic biomass prior to introduction into the pressurized reactor.

It is also disclosed that the process may not comprise a xylans separation step prior to introduction into the pressurized reactor.

It is further disclosed that the process may further comprise a soaking step, wherein the ligno-cellulosic biomass is soaked in a liquid comprised of water prior to introducing the ligno-cellulosic biomass into the pressurized reactor.

It is also disclosed that the process may further comprise an aeration step, wherein the ligno-cellulosic biomass is aerated after the soaking step by exposing the ligno-cellulosic biomass to air.

It is further disclosed that the ligno-cellulosic biomass may be compressed at a compression temperature in a range of 25° C. to less than 100° C. prior to introducing the ligno-cellulosic biomass into the pressurized reactor.

It is also disclosed that the pressurized reactor has a pressurized reactor volume and the vapor head space has a vapor head space volume which may be between 5% and 80% of the pressurized reactor volume.

It is further disclosed that the ligno-cellulosic biomass pressure may be selected so that the refining step steam explodes the ligno-cellulosic biomass.

It is also disclosed that the vapor head space temperature and the residence time may be controlled so that more than 65% of the total amount of xylans are recovered in the pre-treated ligno-cellulosic biomass.

It is further disclosed that the ligno-cellulosic biomass pressure may be controlled so that the pre-treated ligno-cellulosic biomass comprises an amount of accessible glucans and the amount of accessible glucans in the pre-treated ligno-cellulosic biomass relative to the total amount of glucans in the pre-treated ligno-cellulosic biomass is greater than 80%.

DETAILED DESCRIPTION

This invented process relies upon the discovery that the C5 sugars (xylans) do not have to be removed from the ligno-cellulosic biomass prior to steam explosion when a gas is added to the vapor phase. As demonstrated in the experimental section, adding a gas to the vapor phase increases the total pressure used to steam explode the ligno-cellulosic biomass and simultaneously lowers the temperature to the equilibrium steam temperature at the partial pressure of the steam. In this manner, the steam explosion is conducted at a temperature which minimizes the C5 sugar degradation (i.e. very few inhibitors are formed) and the steam explosion is also conducted at a pressure high enough to make the C6 sugars (glucans) accessible to the enzymes. In this manner, the first pressurized reactor of the two stage systems is eliminated, and the steam consumption is dramatically reduced.

It has also been found that by eliminating the first cooking step of the prior art, the air (a gas) entering the steam explosion process with the ligno-cellulosic biomass can be provided in sufficient amounts to carry out the process. This is surprising because removal of air before thermally treating the ligno-cellulosic biomass is almost universally taught in the prior art ranging from paper/pulping textbooks to patents. For example, according to U.S. Pat. No. 4,427,453 to Reitter 1984, one is to use a continuous tube digester with a worm feeder because "[b]y using the worm feeder it is possible to inject into the high pressure reaction space in the digester essentially the shredded material, essentially free of excess liquid, and more importantly, essentially free from air inclusions, which are disadvantageous to the hydrolysis" and "[i]t should be emphasized that an essential point of the process is that with use of a worm press it is possible to remove almost 100% of the air, which is extremely harmful to the hydrolysis, from the chopped biomass, before entry into the digester."

Going opposite of the prior art teachings and conventional wisdom, the inventors have found that by not eliminating the air from the biomass, enough air can be introduced into the system to lower the reactor temperatures and maintain the high pressures required for the simultaneous processing of xylans and glucans in order to recover a large amount of C5 sugars (xylans) and steam explode the ligno-cellulosic biomass to provide extremely high accessibility of the C6 sugars (glucans) to enzymes during the subsequent enzymatic hydrolysis step.

The invented process is a process for producing a bioproduct from a ligno-cellulosic biomass. The process has at least one pressurized reactor which runs continuously. By running continuously, or alternatively operating continuously or operating in a continuous manner it is meant that the ligno-cellulosic biomass is entering the pressurized reactor while at the same time it is being removed from the reactor.

The ligno-cellulosic biomass will be comprised of xylans, glucans, lignin, water and optionally air. The ligno-cellulosic biomass will have a total amount of xylans, a total amount of glucans, and a total amount of lignin on a dry basis. It will also have weight percent water expressed as a percent of the total weight of the ligno-cellulosic biomass which includes the water. The ligno-cellulosic biomass will usually have air either attached to it, dissolved in the water and/or inside the cells of the ligno-cellulosic structure. The ligno-cellulosic biomass can be part of a ligno-cellulosic biomass feedstream.

Xylans are polysaccharides made from units of xylose (a pentose sugar). Xylans are also part of the class of sugars known as the C5's. Xylans contain predominantly linked beta-D-xylose units. The total amount of xylans is the weight amount of xylose equivalents in the ligno-cellulosic biomass.

Glucans are polysaccharides of D-glucose (a hexose sugar) monomers. Glucan's are part of the class of the C6 sugars. The total amount of glucans is the weight amount of glucose equivalents in the ligno-cellulosic biomass.

Lignin is generally thought of as a polymer made from varying amounts of the monolignol monomers of p-coumaryl alcohol, coniferyl alcohol and sinaply alcohol. When present in ligno-cellulose biomass, the term refers term total amount of lignin refers to the weight of the polymers of the three lignol monomers, oligomers of the three lignol monomers and the monomers themselves in the ligno-cellulosic biomass, should they be present.

A detailed description of a ligno-cellulosic feedstock may be found in WO2015028156A1, pg. 11-14, which is herein incorporated by reference. A preferred ligno-cellulosic feedstock is selected from the group of agricultural residues, in particular switchgrass, Mischantus, Arundo Donax, bagasse, such as sugar cane, bagasse, and straws such as wheat straw, rice straw, the hardwoods and softwoods also benefit from this process.

In the process, the ligno-cellulosic biomass comprised of a total amount of xylans, a total amount of glucans and lignin are introduced into a pressurized reactor of a pressurized reactor assembly along with steam and a gas. The pressurized reactor is operated in a continuous manner.

The steam can be part of a liquid water-steam mixture, saturated steam or superheated steam as those terms are known in the art.

While the ligno-cellulosic biomass can enter the pressurized reactor at any temperature, the preferred range is at a temperature in the range of 25° C. to 140° C. immediately prior to entering the pressurized reactor. Because the pressurized reactor operates under a reactor pressure, the ligno-cellulosic biomass generally enters the pressurized reactor under a pressure at least as great, or preferably greater, than the pressure of the pressurized reactor. Compression is often applied to the ligno-cellulosic biomass by a compression device, such as a plug screw feeder, to drive off water and increase the pressure for entry into the pressurized reactor. It is preferable that the ligno-cellulosic biomass is introduced into the compression device at a compression temperature of less than 100° C., and with a compression temperature preferably in the range of 25° C. to less than 100° C., with a compression temperature in the range of 25° C. to 95° C. more preferred with a compression temperature in the range of 30° C. to 90° C. most preferred.

The pressurized reactor can be a horizontal reactor, a vertical reactor or a tilted or slanted reactor, also known as an inclined reactor, with the ligno-cellulosic biomass flowing in any direction (uphill or downhill or perpendicular to, relative to the force of gravity).

The pressurized reactor is operated at conditions to have a vapor head space in the pressurized reactor. This means the reactor is not operated with 100% of its volume full of ligno-cellulosic biomass. The vapor head space of a pressurized reactor is a well-known term in the art referring to a portion of the reactor above the liquid and/or solids (the ligno-cellulosic biomass) in the reactor. There are very few liquids or solids in the vapor head space of the pressurized reactor save for the liquid, (e.g. water) which may be condensing on the walls of the reactor or parts of the internals such as an agitator shaft(s) or conveying screw(s) which rise(s) above the level of the ligno-cellulosic biomass in the reactor and is in the vapor head space.

The vapor head space has a volume, called the vapor head space volume, which is expressed as a percent of the volume of the pressurized reactor. The volume of the pressurized reactor is called the pressurized reactor volume. Typical vapor head space volumes are in the ranges of 5% to 80% of the pressurized reactor volume, with 10% to 80% of the pressurized reactor volume more preferred, with 15% to 75% of the pressurized reactor volume even more preferred, 25% to 75% of the pressurized reactor volume, also preferred, and with 35% to 65% of the pressurized reactor volume most preferred.

The gasses used in this process are gasses which are not vapors at the temperature and pressure conditions of the pressurized reactor. Steam exists as a vapor. That is steam exists in equilibrium with the liquid water present in the pressurized reactor, as steam is a vapor it is not a gas. The gas being introduced does not have a vapor in equilibrium with a corresponding liquid in the reactor. Thus the gas does not condense at the temperature and pressure of the vapor head space. Typical gasses of this type include but are not limited are nitrogen, oxygen, carbon dioxide and many volatile organic compounds. The term gas also includes mixtures comprising gasses which do not form a liquid phase in equilibrium with the gas, such as air.

The pressurized reactor is part of a reactor assembly. The reactor assembly will typically include a feeding device for loading the ligno-cellulosic biomass into the pressurized reactor. The feeding device may be operated continuously or in aliquots or pulses, the process being a continuous process because the ligno-cellulosic biomass is entering the pressurized reactor while at the same time ligno-cellulosic biomass is being removed from the reactor. A compression screw and rotary air-lock valve are examples of feeding devices well known in the art. The reactor assembly will also have a discharge device for discharging or removing the ligno-cellulosic biomass from the reactor. The discharge device is selected so as to rapidly release the ligno-cellulosic biomass pressure and refine the ligno-cellulosic biomass.

Refining the ligno-cellulosic biomass means reducing the size. Refining by rapidly reducing the pressure can be done to cause cells of the ligno-cellulosic biomass to burst, that is steam explode. This is also known that the refining step steam explodes the ligno-cellulosic biomass. These processes have been used since the 1930's with the invention of the Masonite gun.

When the steam enters the pressurized reactor, at least a portion of the steam will condense to liquid water on the ligno-cellulosic biomass. In this manner, the latent heat of vaporization is transferred from the steam to the ligno-cellulosic biomass to increase the temperature of the ligno-cellulosic biomass. The condensing of the steam onto the biomass establishes the vapor liquid equilibrium distinguishing steam from a gas. Steam exists as a vapor in equilibrium with its liquid water form. The gas has no liquid form at the reactor conditions.

Accordingly, it can be said that the first step of the process is introducing the ligno-cellulosic biomass, a total amount of gas, and steam into a pressurized reactor of a pressurized reactor assembly operated at conditions to have a vapor head space in the pressurized reactor, wherein a portion of the steam condenses on the ligno-cellulosic biomass.

The point of introduction does not have to be the same point for each of the elements. The steam could enter from the reactor top, the reactor bottom, the reactor sides, or all locations at the same time. The gas could enter the reactor in the same manner.

Preferably, when the gas enters as air, it enters as part of the ligno-cellulosic biomass as entrapped air. Entrapped air is the air which is inside the cells of the ligno-cellulosic biomass, dissolved in the water o the ligno-cellulosic biomass, or attached or adhered to the ligno-cellulosic biomass.

The next step of the process is to hold or maintain the ligno-cellulosic biomass in the pressurized reactor for a residence time from 0.5 minutes to 120 minutes at a vapor head space temperature in a range of 130° C. to 230° C. Preferably, residence time is in a range from 1 minute to 60 minutes, more preferably from 1 minute to 30 minutes, and most preferably from 1 minute to 15 minutes. The vapor head space temperature is preferably in a range from 150° C. to 220° C., more preferably from 160° C. to 210° C., and most preferably from 170 to 200° C.

The term residence time refers to the elapsed time between the ligno-cellulosic biomass entering the reactor and the ligno-cellulosic biomass exiting (discharging from) the reactor. There is a lot of latitude in the selection of the residence time. The lower temperature would allow for a longer residence time for optimal yields while the higher temperatures mandate a lower residence time to avoid degradation of the xylans.

The vapor head space temperature at a given vapor head space pressure may be controlled by varying the amount of gas relative to the amount of steam in the vapor head space. In the case that air is introduced as part of the ligno-cellulosic biomass or ligno-cellulosic feedstream, the amount of air relative to the amount of steam in the vapor head space may be varied by varying the volume of the vapor head space, that is, the filling factor of the pressurized reactor. Thereby, also the filling factor of the pressurized reactor may be used as a control parameter to a certain extent. The reference is to the vapor head space temperature which, for the most part, is the same temperature as the temperature of the water vapor condensing onto the ligno-cellulosic biomass. In this manner, the heat of vaporization is released upon the surface of the ligno-cellulosic biomass particles. Due to heat transfer characteristics of the ligno-cellulosic biomass, the ligno-cellulosic biomass will increase in temperature as it passes through the pressurized reactor. Computer simulations and in plant experiments can be used to determine the heat up rate as the ligno-cellulosic biomass increases in temperature from the ligno-cellulosic biomass entry temperature when it enters the pressurized reactor and approaches the temperature of the condensing steam.

Depending upon where the steam enters the pressurized reactor, the steam will condense on the ligno-cellulosic biomass upon contact. If the steam is condensing on top of the ligno-cellulosic biomass in the vapor head space, the water will run down into the ligno-cellulosic biomass. If the steam is condensing in the bottom of the pressurized reactor, some of the steam condenses and the remainder continues to pass through the ligno-cellulosic biomass as it travels upward to the vapor head space. The temperature of the ligno-cellulosic biomass will increase during the residence time as the ligno-cellulosic biomass moves through the reactor. Accordingly, the ligno-cellulosic biomass may never reach the vapor head space temperature.

The implications of this temperature profile are that the traditional treatment parameters of severity are only a first order estimate of the thermal treatment in a continuous process.

The vapor head space will have a vapor head space pressure. The vapor head space will operate at this vapor head space pressure which is the pure steam's equilibrium pressure at the vapor head space temperature plus the partial pressure of the gas at the vapor head space temperature. The vapor head space temperature at a fixed the vapor head space pressure will drop as the amount of gas in the vapor head space is increased. By adding the gas into the pressurized reactor the temperature and pressure have been decoupled from the pure steam equilibrium conditions.

This is best described in the following table demonstrating how the amount of gas influences the temperature at a fixed vapor head space pressure, or ligno-cellulosic biomass pressure of 23 bar. Reference gas is air.

TABLE 1

EFFECT OF GAS ON VAPOR HEAD SPACE TEMPERATURE

| Vapor Head Space Temperature (° C.) | Pure steam's equilibrium pressure at the vapor head space temperature (bar) (partial pressure) | Gas Pressure at 23 Bar Vapor Head Space Pressure (bar) | Mole % Steam Vapor | Mole % Gas |
|---|---|---|---|---|
| 140 | 3.6 | 19.4 | 15.7 | 84.3 |
| 150 | 4.8 | 18.2 | 20.9 | 79.1 |
| 160 | 6.2 | 16.8 | 27.0 | 73.0 |
| 170 | 7.9 | 15.1 | 34.3 | 65.7 |
| 180 | 10.2 | 12.8 | 44.3 | 55.7 |
| 185 | 11.2 | 11.8 | 48.7 | 51.3 |
| 190 | 12.6 | 10.4 | 54.8 | 45.2 |
| 195 | 14 | 9 | 60.9 | 39.1 |
| 200 | 15.5 | 7.5 | 67.4 | 32.6 |
| 205 | 17.2 | 5.8 | 74.8 | 25.2 |
| 210 | 19 | 4 | 82.6 | 17.4 |
| 215 | 21 | 2 | 91.3 | 8.7 |
| 220 | 23 | 0 | 100.0 | 0.0 |

As readily seen, by maintaining the gas at 84.3 mole % of the vapor head space with the remainder of the vapor head space being steam (i.e. a vapor), the temperature of the 23 bar vapor head space can be controlled at 140° C.

The vapor head space pressure, which is greater than the pure steam equilibrium pressure at the vapor head space temperature, is equal to the ligno-cellulosic biomass pressure as the static pressure of the ligno-cellulosic biomass across its bed height is negligible and is ignored for the purposes of this process. Because the pressure and temperature are no longer coupled according to pure steam equilibrium, the vapor head space pressure, which is equal to the ligno-cellulosic biomass pressure, is to be at least 0.5 bar greater than pure steam's equilibrium pressure at the vapor head space temperature. While 0.5 bar is a minimum difference, greater than 1 bar is more preferred with greater than 1.5 bar being more preferred, with greater than 2 bar being more preferred with as great as 6 bar being most preferred.

The vapor head space pressure in the pressurized reactor, which is also the ligno-cellulosic biomass pressure, should be at least 10 bar as to best facilitate the refining step and better steam explode the ligno-cellulosic biomass, with at least 13 bar being preferred, at least 15 bar even more preferred, and 18 bar most preferred. It is the steam explosion which makes the glucans more accessible to the enzymes when the steam exploded ligno-cellulosic biomass is passed into the saccharification/enzymatic hydrolysis phase. Even if one of the advantages of the disclosed process is to operate at a very high vapor head space pressure i.e. without degrading sugars, it is preferred that the vapor head space pressure which is also the ligno-cellulosic biomass pressure, is less than 30 bar for practical reasons, as for instance avoiding excessive costs of the pressurized reactor. Thereby the vapor head space pressure, which is also the ligno-cellulosic biomass pressure, may be in a range of 10 to 30 bar, or 13 to 30 bar, or 15 to 30 bar, or 18 to 30 bar.

The residence time is controlled, for example, by controlling the rotational speed of a conveying screw in a horizontal reactor. The residence time can also be controlled by controlling the amount of ligno-cellulosic biomass entering the pressurized reactor.

One of ordinary skill will realize that by controlling the rate of the biomass through the reactor, the amount of steam, the amount of gas, the agitation or surface renewal of the biomass, and the particle size of the biomass, one can reach an optimal pretreatment residence time at a given vapor head space temperature and vapor head space pressure (i.e. ligno-cellulosic biomass pressure).

One of ordinary skill can control the vapor head space temperature and the residence time as discussed earlier so that more than 65% of the total amount of xylans are recovered in the pre-treated ligno-cellulosic biomass exiting the reactor assembly. Recovered means that one measures the amount of xylan equivalents in the pre-treated ligno-cellulosic biomass on a dry basis and expresses the amount as a percent of the total amount of xylan equivalents in the ligno-cellulosic biomass prior to a reference point which in this case is prior to entering the pressurized reactor. Procedure for measuring the amount of xylans in the ligno-cellulosic biomass to calculate xylans recovery is set out in the experimental section. For example, if one grinds the ligno-cellulosic biomass and measures 200 kg of total xylans (expressed as xylan equivalents) in a ton of ligno-cellulosic biomass on a dry basis immediately before entering the pressurized reactor, an 65% xylans recovery means that there are 130 kg xylans (expressed in xylan equivalents) per ton of the pre-treated ligno-cellulosic biomass. While 65% recovered xylans is an achievable amount, the data in the experimental section demonstrates that this process is capable of achieving at least 70% recovered xylans, with at least 75% recovered xylans more preferred and at least 80% recovered xylans being the most preferred.

If 80% of the initial amount of xylans are recovered, then the maximum of xylans which is degraded is 20%.

Accordingly the second step of the process can be described as maintaining the ligno-cellulosic biomass in the pressurized reactor at a ligno-cellulosic biomass pressure for a residence time from 0.5 minutes to 120 minutes, at a vapor head space temperature in a range of 130° C. to 230° C.; wherein the temperature of the vapor head space and the residence time are controlled so that more than 65% of the total amount of xylans are recovered in the pre-treated ligno-cellulosic biomass.

The third step of the process is to refine the ligno-cellulosic biomass. Refining the ligno-cellulosic biomass means to reduce the size of the ligno-cellulosic particle. In the process refining is done by rapidly releasing the ligno-cellulosic biomass pressure while discharging the ligno-cellulosic biomass from the pressurized reactor assembly to create a pre-treated ligno-cellulosic biomass. When the pressure drop is high enough, the ligno-cellulosic biomass will explode. That is the pressure drop is so quick and great that the cells of the ligno-cellulosic biomass undergo a process known as steam explosion. As indicated in the experimental section, in this process the high pressures required for good accessibility of the glucans to enzymes in the enzymatic hydrolysis step can be achieved without having to be associated with the high steam temperatures historically associated with those high pressures. In this manner the C5 sugars (xylans) are not degraded, but recovered and the C6 sugars (glucans) are made accessible. This steam explosion uses a discharge device designed for steam explosion. Steam explosion discharge devices are well known in the art as steam explosion technology has existed for decades.

Accordingly, the third step can be described as refining the ligno-cellulosic biomass by rapidly releasing the ligno-cellulosic biomass pressure while discharging the ligno-cellulosic biomass from the pressurized reactor assembly, to create a pre-treated ligno-cellulosic biomass.

After reading this specification, one of ordinary skill should appreciate that the pre-treated ligno-cellulosic biomass comprises an amount of accessible glucans and the amount of accessible glucans in the pre-treated ligno-cellulosic biomass relative to the total amount of glucans in the pre-treated ligno-cellulosic biomass is greater than 80%.

The amount of accessible glucans in the pre-treated ligno-cellulosic biomass is defined as the amount of glucans which are made available to enzymatic hydrolysis and can be converted to glucose for fermentation. The accessible glucans are measured as defined in the experimental section. The total amount of glucans in the pre-treated ligno-cellulosic biomass is self-explanatory and determined according to the method defined in the experimental section.

Since it is primarily the amount of pressure released that determines the glucans accessibility one of ordinary skill controls the ligno-cellulosic biomass pressure (i.e. the vapor head space pressure) so that the pre-treated ligno-cellulosic biomass comprises an amount of accessible glucans and the amount of accessible glucans in the pre-treated ligno-cellulosic biomass relative to the total amount of glucans in the pre-treated ligno-cellulosic biomass is greater than 80%. The ligno-cellulosic biomass pressure is the same as the vapor head space pressure which is the sum of the equilibrium pressure of steam at the vapor head space temperature and the partial pressure(s) of the gas(es) in the vapor head space at the vapor head space temperature. As shown earlier, this vapor head space pressure is thus determined by the amount of gas in the vapor head space and the amount of steam in the vapor head space.

It has also been discovered that the ligno-cellulosic biomass can be introduced as a ligno-cellulosic biomass feedstream comprising air thus avoiding the air elimination step historically believed essential, and that a percent amount of the gas introduced as part of the ligno-cellulosic biomass feedstream is at least a value selected from the group consisting of 50%, 70%, and 90%, or even 100% of the total amount gas introduced into the pressurized reactor.

It is even feasible, as shown in the experimental section for all of the gas, such as air, to be introduced as part of the ligno-cellulosic biomass or ligno-cellulosic feedstream. Stated differently, all the gas is derived in-situ, and the gas is not added separately to the feedstream or pressurized reactor. It is believed that introducing air entrapped within the ligno-cellulosic biomass may further improve the refining step of the ligno-cellulosic biomass with respect to add air, or gas, from a separated inlet, as the presence of air may result in more effective explosion of the cells.

A further embodiment of the process further comprises soaking the ligno-cellulosic biomass in a liquid comprised of water prior to introducing the ligno-cellulosic biomass into the pressurized reactor. The soaking step is well known in the art and can be done at many different soaking temperatures and pressures. The ligno-cellulosic biomass may be dewatered prior to being introduced into the pressurized reactor. Preferably, soaking is done at a temperature less than 100° C. and at atmospheric pressure to avoid the use of expensive pressurized equipment or vacuum.

At soaking temperatures below 100° C., the hemi-cellulose (xylans) will not dissolve very much and most, if not all, will pass with the ligno-cellulosic biomass into the pressurized reactor. Additionally, soaking at atmospheric pressure and temperature less than 100° C. keeps the air entrained in the ligno-cellulosic biomass so that the air may enter the pressurized reactor with the ligno-cellulosic biomass.

The preferred soaking procedure is conducted with the ligno-cellulosic biomass in contact with air. This may be accomplished by introducing the ligno-cellulosic biomass into a soaking pool or vessel filled with water, with the free surface of water exposed to atmospheric air. The ligno-cellulosic biomass, which has typically a density less than water, will float on the water surface and may be periodically submerged by mechanical means, thereby wetting the ligno-cellulosic biomass at the same time maintaining air and xylans with the ligno-cellulosic biomass. If there is an optional soaking step, it is preferable to maintain the operating conditions so that less than 15% by weight of the xylans are separated from the ligno-cellulosic biomass before the ligno-cellulosic biomass is introduced in the pressurized reactor, preferably less than 10% by weight of the xylans are separated from the ligno-cellulosic biomass before the ligno-cellulosic biomass is introduced in the pressurized reactor, and more preferably less than 5% by weight of the xylans are separated from the ligno-cellulosic biomass before the ligno-cellulosic biomass is introduced in the pressurized reactor, with no xylans being separated from the ligno-cellulosic biomass before the ligno-cellulosic biomass is introduced in the pressurized reactor being the most preferred.

While a xylans separation step is optional, it is preferable that the xylans are not separated from the ligno-cellulosic biomass prior to introducing the ligno-cellulosic biomass into the pressurized reactor so as to eliminate the cost and complexity of the equipment associated to that separation step. If there is an optional xylans separation step prior to the ligno-cellulosic biomass being introduced into the pressurized reactor, it is preferable to maintain the operating conditions of the xylans separation step such that less than 15% by weight of the xylans are removed from the ligno-cellulosic biomass before the ligno-cellulosic biomass is introduced in the pressurized reactor, preferably less than 10% by weight of the xylans are removed from the ligno-cellulosic biomass before the ligno-cellulosic biomass is introduced in the pressurized reactor, and more preferably less than 5% by weight of the xylans are removed from the ligno-cellulosic biomass before the ligno-cellulosic biomass is introduced in the pressurized reactor, with no xylans being removed from the ligno-cellulosic biomass before the ligno-cellulosic biomass is introduced in the pressurized reactor being the most preferred.

It has also been discovered in one embodiment that the ligno-cellulosic biomass can be introduced into the pressurized reactor as a ligno-cellulosic biomass feedstream comprising the ligno-cellulosic biomass and air, wherein the air is the gas. This air can be entrained in the biomass and never removed before entering the pressurized reactor, or the air can come from aerating the biomass after being soaked. An exemplary embodiment of such aeration step is described in the experimental section but the simplest form is to expose the biomass to air or the atmosphere. Aeration time is preferably greater than 10 seconds, more preferably greater than 30 seconds, and most preferably greater than 60 seconds. While there is not an upper limit for aeration, it is preferred that aeration time is less than 1 hour. Eventually, the aeration step may comprise exposing the soaked biomass to a forced flow of air.

In a preferred embodiment, the soaked ligno-cellulosic biomass is subjected to a dewatering step prior to being introduced into the pressurized reactor. Dewatering may comprise a draining step under the effect of gravity force to remove at least a portion of the free water or liquid, and a compression step to remove at least a portion of the soaked liquid in the ligno-cellulosic biomass. The aeration step is preferably conducted in all or in part after the compression step and it may comprise softening the ligno-cellulosic biomass, that is fluffing up the ligno-cellulosic biomass for reducing the volumetric density with respect to the volumetric density at the end of the compression step. The softening of the compressed ligno-cellulosic biomass may be obtained by means of a mechanical action, such as for instance a distribution screw. While air is the preferred gas, the process may further comprise introducing an additional gas which is not air into the pressurized reactor. In fact, in one embodiment, the air is atmospheric air in at least one of the ligno-cellulosic biomass or the water and the ligno-cellulosic biomass and the water have not been subjected to an air removal step prior to being introduced into the pressurized reactor.

There are many ways to convey the ligno-cellulosic biomass through the reactor and one way is wherein the ligno-cellulosic biomass is mechanically conveyed from an inlet of the pressurized reactor to an outlet of the pressurized reactor. After producing the pre-treated ligno-cellulosic biomass stream, the ligno-cellulosic biomass is exposed to at least one hydrolysis catalyst such as an enzyme or metal in order to hydrolyze at least a portion of the glucans to glucose. This hydrolysis step is well known in the art and when enzymes are used it is referred to enzymatic hydrolysis.

After hydrolyzing at least a portion of the glucans to glucose, at least a portion of the glucose is converted to a bio-product. The most commonly known bio-product is bio-ethanol produced by placing the glucose in the presence of a yeast. This technology to convert glucose to a bio-product, such as bio-ethanol is well known. For example wine and beer are made by converting the glucose to ethanol. Oftentimes for industrial purposes, as opposed to consumption purposes like beer and wine, the bio-ethanol is distilled and purified.

A detailed description of hydrolysis and fermentation processes is for instance contained in Handbook on bioethanol: Production and utilization", Charles E. Wyman, Taylor and Francis, 1996.

EXPERIMENTAL

The ligno-cellulosic biomass used in the reported experiments was raw wheat straw with a dry matter of 90% by weight.

Three different experimental set-ups were used to demonstrate the advantages of the disclosed process.

First Experimental Set-Up (Control)

The first experimental set-up subjected the ligno-cellulosic biomass to a two-step continuous pretreatment process, wherein xylans are solubilized in the first pretreatment step conducted at mild conditions in the first pressurized reactor, then a liquid comprising water and solubilized xylans was separated from the ligno-cellulosic biomass prior to subjecting the xylans depleted ligno-cellulosic biomass to a second pretreatment step at severe conditions in the second pressurized reactor, and to a steam explosion step. The first experimental set-up operated the whole process under pressurized conditions, thereby preventing the ligno-cellulosic biomass to contact atmospheric air over the whole process and specifically before the second pretreatment step in the second pressurized reactor, according to the general teaching of WO 2009/108773.

The first pressurized reactor was a vertical reactor. The ligno-cellulosic biomass was continuously introduced from the top of the first pressurized reactor and subjected to a pretreatment step by introducing steam. The first pressurized reactor was pressurized by steam. The ligno-cellulosic biomass was introduced in the first pressurized reactor through a pre-steamer, which is a standard apparatus and procedure used in wood pulp system to pre-condition the ligno-cellulosic biomass with steam and remove entrapped air. Thereby, in the first pressurized reactor air, if present, was in very limited amount. The first pre-treatment step was conducted at mild temperature conditions (see table 2) sufficient to solubilize xylans of the ligno-cellulosic biomass with limited xylans degradation. The ligno-cellulosic biomass was removed from the bottom of the first pressurized reactor in the form of a slurry with a dry matter of 5%, and it flowed then under pressurized conditions to the second pressurized reactor. Between the first and the second pressurized reactor, free liquid was extracted from the ligno-cellulosic biomass slurry by draining under gravity in an inclined drainer, operated in steam pressurized conditions at about the same pressure and temperature of the first pressurized reactor. The free liquid separated from the ligno-cellulosic biomass, comprising water and solubilized xylans, was collected in a tank. The drained, xylans depleted ligno-cellulosic biomass was continuously inserted in the second pressurized reactor, which was a horizontal cylindrical reactor, by means of a plug screw feeder, subjecting the ligno-cellulosic biomass to shear and compression forces to continuously form a ligno-cellulosic biomass plug capable of maintaining a difference of pressure between the pressurized reactor and the inlet of the plug screw feeder which was at about the steam pressure of the first pressurized reactor. The temperature of the ligno-cellulosic biomass at the inlet of the plug screw feeder was about the same temperature of the first pressurized reactor and the dry matter content was about 15%.

A portion of the soaked liquid in the ligno-cellulosic biomass, comprising water and solubilized xylans, was removed by the plug screw feeder and collected. Soaked liquid is the liquid contained in the ligno-cellulosic biomass which needs a certain mechanical action to be removed, in spite of the free liquid which is removed by gravity. In the second pressurized reactor, the xylans depleted ligno-cellulosic biomass entered at a dry matter of about 45% and was pre-treated by inserting saturated steam through a set of steam inlets distributed on the lateral surface of the second pressurized reactor. The steam flow was regulated in a ratio of 1:1 with the ligno-cellulosic biomass flow entering the reactor, by weight per hour on a dry basis. The pressure of the steam before entering the reactor, measured on the back of one steam inlet, was 21 bar, and the corresponding steam temperature was 216° C. In the second pressurized reactor, the ligno-cellulosic biomass was subjected to more severe temperature conditions for a shorter residence time than in the first pressurized reactor (see Table 2). The ligno-cellulosic biomass was conveyed from the inlet to the outlet of the horizontal second pressurized reactor by means of a screw internal to the reactor, and the residence time was controlled by changing the rotation speed of the screw. The second pressurized reactor was operated at a fill factor of about 30%, and the temperature and pressure of the vapor head space of the reactor were constantly measured. After the second pre-treatment step in the second pressurized reactor, the ligno-cellulosic biomass was steam exploded through a blow line connected to the reactor outlet and recovered in a blow cyclone at a pressure of about 0.5 bar.

Second Experimental Set-Up

In the second experimental setup, the pre-treatment system of the first experimental set-up was operated to subject the ligno-cellulosic biomass to a soaking step in water at a temperature less than 100° C. and in contact with atmospheric air, to increase the moisture content of the ligno-cellulosic biomass and remove some of the non-ligno-cellulosic components of the ligno-cellulosic biomass. The non-ligno-cellulosic components of the ligno-cellulosic biomass comprise extractives such as salts, waxes, and proteins, and external contaminants from the harvesting step, such as dust, stones, and metallic debris. No xylans were extracted in the soaking step due to the low soaking temperature. Then, a liquid comprising water and the removed non-ligno-cellulosic components was separated from the ligno-cellulosic biomass prior to subjecting the soaked ligno-cellulosic biomass to a unique pretreatment step at severe conditions in a pressurized reactor, and to a steam explosion step. The second experimental setup comprises one pressurized reactor and the ligno-cellulosic biomass was allowed to enter in contact with air before being introduced in the pressurized reactor, which was the second pressurized reactor of the first experimental set-up.

The ligno-cellulosic biomass was inserted into the first vertical reactor of the first experimental set-up, which was operated in not steam-pressurized conditions. In the first vertical reactor, which was thereby operated as a soaking vessel, the ligno-cellulosic biomass was subjected to a soaking step for a soaking time of 40 minutes, at a temperature less than 100° C. and 1 bar by inserting steam. The soaking vessel was operated at a filling factor about 30% and it was not sealed from external atmosphere, thereby air was present in the top portion of the soaking vessel. Thereby, in the soaking vessel the ligno-cellulosic biomass was subjected to a limited exposure to air during the soaking step. The ligno-cellulosic biomass was removed from the bottom of the soaking vessel in the form of slurry at a dry matter of 5%, and it flowed then at atmospheric pressure to the unique pressurized reactor of the second experimental set-up. Between the soaking vessel and the pressurized reactor, free soaking liquids were extracted from the ligno-cellulosic biomass slurry by draining under gravity in the inclined drainer, which was also operated in contact with atmospheric air. Free soaking liquid, comprising water, external contaminants and extractives of the ligno-cellulosic biomass, was withdrawn from the process. No xylans were detected in the removed liquids. The drained solid ligno-cellulosic biomass, together with entrapped air, was inserted in the pressurized reactor by means of the plug screw feeder, with a portion of the soaked liquid being removed by the plug screw feeder and withdrawn from the process. The temperature of the ligno-cellulosic biomass at the inlet of the plug screw feeder was 80° C. and the dry matter was about 15%. The soaked liquid comprises water, external contaminants and extractives of the ligno-cellulosic biomass, and no xylans. The ligno-cellulosic biomass entered the pressurized reactor at a dry matter of about 45%.

A portion of the air entrapped in the ligno-cellulosic biomass, but not all, may have been removed by the plug screw feeder together with a portion of the soaked liquid. Namely, in a preliminary test, the density of the ligno-cellulosic biomass plug close to the outlet of the plug screw feeder was significantly less than the density of a highly densified sample separately produced by compressing the soaked ligno-cellulosic biomass.

In the pressurized reactor, the soaked ligno-cellulosic biomass was pre-treated by inserting saturated steam with the same procedure detailed in the first experimental set-up. After the pre-treatment step in the pressurized reactor, the ligno-cellulosic biomass was steam exploded through the blow line and recovered in the blow cyclone at a pressure of about 0.5 bar.

In the second experimental set-up, the drained solid ligno-cellulosic biomass was exposed to air also in the inclined drainer and till being introduced in the plug screw feeder. Exposure to air was nevertheless at a limited extent, as the ligno-cellulosic biomass was compacted by effect of gravity in the soaking vessel and the inclined drainer.

The whole process was operated continuously.

Third Experimental Set-Up

The third experimental setup comprised the soaking vessel of the second experimental set-up (i.e. the first vertical reactor of the first experimental setup operated at atmospheric pressure in contact with air), a system operated in atmospheric air for dewatering and aerating the soaked ligno-cellulosic biomass and the horizontal pressurized reactor described in previous experimental set-ups. With respect to the second experimental setup, the third experimental set-up was designed to increase the exposure of the ligno-cellulosic biomass to air after the soaking step and before introducing the ligno-cellulosic biomass into the pressurized reactor, thereby to increase the amount of air introduced in the pressurized reactor together with the ligno-cellulosic biomass.

First, the ligno-cellulosic biomass was subjected to a soaking step as described in the second experimental setup. Before inserting the ligno-cellulosic biomass into the pressurized reactor, free liquid and a portion of the soaked liquid were sequentially removed in a multi-step dewatering process. During dewatering, the ligno-cellulosic biomass was subjected to aeration by exposure to atmospheric air in order to increase the amount of air entrapped in the biomass. First, free liquid was removed by draining under gravity through a perforated horizontal surface (belt). During this step, no mechanical actions other than gravity were exerted on the ligno-cellulosic biomass to avoid closing the pores of the ligno-cellulosic biomass. The ligno-cellulosic biomass was distributed by means of a first horizontal distribution screw on the perforated horizontal surface to drain free liquid. The horizontal distribution screw was operated to equalize the height of the ligno-cellulosic biomass without exerting significant compression, in order to increase the surface of the ligno-cellulosic biomass exposed to air and the amount of air entrapped in the biomass. Then, a portion of the soaked liquid was removed from the ligno-cellulosic biomass by compression in a belt filter press. After the compression step, the ligno-cellulosic biomass was distributed on a horizontal surface and fluffed by means of a second horizontal distribution screw, thereby it was subjected to a second aeration step. The time for conducting the dewatering and aeration procedure was varied, and the minimum time was 1 minute. The ligno-cellulosic biomass, with air entrapped in the pores, was continuously inserted into the horizontal pressurized reactor by means of the plug screw feeder. The temperature of the ligno-cellulosic biomass at the inlet of the plug screw feeder was 70° C. and the dry matter was 22%. In the plug screw feeder, a further portion of soaked liquid was removed and the ligno-cellulosic biomass entered the pressurized reactor at a dry matter of about 45%.

As in the second experimental set-up, in a preliminary test, the density of the ligno-cellulosic biomass plug close to the outlet of the plug screw feeder was significantly less than the density of a highly densified sample separately produced by compressing the soaked ligno-cellulosic biomass. Thereby, a portion of the air entrapped in the ligno-cellulosic biomass, but not all, may have been removed by the plug screw feeder.

In the pressurized reactor, the soaked ligno-cellulosic biomass was pre-treated by inserting saturated steam with the same procedure detailed in the first and second experimental set-ups. After the pre-treatment step in the pressurized reactor, the ligno-cellulosic biomass was steam exploded through the blow line and recovered in the blow cyclone at a pressure of about 0.5 bar.

Comparison of the Three Experimental Set-Ups and Related Processes

The different experimental set-ups were operated continuously in different runs, for run times as long as to 3 days. After an initial start-up transitory phase, which was different for each experimental set-up, a steady state was reached.

The first experimental set-up failed to work for long run time, being frequently stopped after few hours of operation due to plugging of the ligno-cellulosic biomass in the pressurized sections between the first and the second pressurized reactors. The second and third experimental set-ups did not present any kind of plugging problems.

The temperature of the vapor head space and the residence time measured in steady conditions were used to calculate the severity factor R0 of the processes of the second and third experimental set-ups according the well-known formula:

$$\mathrm{Log}(R0)=\mathrm{Log}[t*\exp[T-100/14.75]],$$

wherein t is the residence time in minutes and T is the temperature of the vapor head space.

In the case of the first experimental set-up, the severity factor also included first pre-treatment step, taking into account the corresponding residence time and temperature in the first pressurized reactor. As discussed in detail previously, the severity factor of the process is a first order estimate of the severity factor experienced by the ligno-cellulosic biomass.

The different processes were evaluated in terms of xylans recovery and glucans accessibility.

Xylans recovery is the percent ratio of the total amount of xylose equivalents in the pre-treated ligno-cellulosic biomass and the amount of xylose equivalents present in the ligno-cellulosic biomass at a specified reference point in the process. The complementary to 100% of the xylose recovery represents therefore the total amount of xylans degraded to degradation products as an effect of the pretreatment process.

The compositions of the ligno-cellulosic biomass and pretreated ligno-cellulosic biomass, in terms of moisture content, glucose, xylose, cellobiose, xylobiose, xylo-oligomers, gluco-oligomers, insoluble glucans and insoluble xylans, was measured according to the NREL methods NREL/TP 510 42618, NREL/TP 510 42623, NREL/TP 510 42621, NREL/TP 510 42620. All the streams produced in the different experimental setups were taken into account in the mass balance. All the sugars different from monomeric xylose were converted to xylose equivalents taking into account the corresponding molecular weights. In all the three experimental set-ups, the reference point was immediately before entering the whole process, that is the xylans recovery was calculated relative to the ligno-cellulosic biomass entering the process.

Glucans accessibility is defined as the percent amount of total soluble glucans at the end of a reference enzymatic hydrolysis (including thereby monomers and soluble oligomers) with respect to the amount of total glucans in the pre-treated ligno-cellulosic biomass, when the reference enzymatic hydrolysis is conducted with a fixed excess of enzymes for a fixed time. All the sugars different from monomeric glucose were converted to glucose equivalent taking into account the corresponding molecular weights.

Glucans accessibility represents the maximum percent of glucans which can be recovered in soluble form in a hydrolysis process of the pretreated ligno-cellulosic biomass Glucans accessibility was determined according to the following procedure.

Pretreated material was mixed with water in a volume of 1500 ml to obtain a mixture having a 7.5% dry matter content and the mixture was inserted into an enzymatic reactor. pH was set to 5.2 and temperature was set to 50° C. An enzyme cocktail (CTec3EU by Novozymes) was added, corresponding to a concentration of 12 g of cocktail solution per 100 gram of solid contained in the mixture. Enzymatic hydrolysis was carried out for 48 hours under agitation. The content of glucans, glucose and glucooligomers in the mixture was measured by standard HPLC analysis.

Table 2 presents the operating parameters at steady state and corresponding severity factors of exemplary process runs of the three experimental set-ups, and the performance of the total process in terms of xylans recovery and glucans accessibility.

Relative to the first pretreatment step/soaking step of the experimental setups, the percent amount of solubilized xylans in the liquid streams separated from the ligno-cellulosic biomass is also reported. It is noted that the soaking step of the second and third experimental setup does not separate xylans, while in the first experimental set-up some xylans are separated from the ligno-cellulosic biomass, depending on the severity of the first pretreatment step.

Relative to the second pretreatment step/unique pretreatment step of the experimental setups, it is reported also the pressure that would be measured if only pure steam would be present in the vapor head space. Delta P represents the additional pressure which is measured in the vapor head space, with respect to the case of pure steam. In the two runs of the first experimental setup (second pretreatment step), the measured pressure corresponds to the pressure of pure steam at the measured temperature, thereby only steam is present in the vapor head space of the second pressurized reactor of the first experimental set-up.

The first run of the first experimental setup, wherein the first pre-treatment step was conducted at a higher temperature than the second run, shows high xylans recovery of 87%. A higher amount of xylans were extracted in the first pre-treatment step and the low amount of remnant xylans in the ligno-cellulosic biomass were subjected to degradation in the second pretreatment step, due also to the lower temperature in the second pretreatment step. Unfortunately, due to this low temperature, the glucans accessibility was only 83%, as the low steam pressure present in the second pressurized reactor was not effective in steam explosion. The high temperature in the second pre-treatment step increases glucans accessibility, but the overall xylans recovery decreases due to a higher amount of remnant xylans degraded at this higher temperature.

The second run of the first experimental setup, wherein the first pre-treatment step was conducted at quite low temperature, shows low xylans recovery of 64%. As a relevant amount of xylans were thereby not removed, they were degraded in the second pretreatment step conducted at high temperature, corresponding to the steam temperature at the measured vapor head space pressure. Glucans accessibility was 88% indicative of an effective steam explosion.

In both the second and third experimental setups, the measured vapor head space pressure significantly exceeded the pressure of pure steam at the measured head space temperature, indicating that entrapped air was introduced in the pressurized reactor with the ligno-cellulosic biomass giving an additional contribution to the total pressure present in the vapor head space. It is noted that the additional pressure is about 2 bar in the second experimental setup and exceeding 6 bar in the third experimental set-up, corresponding to a greater aeration in the latter case. The amount of air present in the vapor head space could be calculated by means of Dalton's law of partial pressures. Nevertheless, also in the case of the second experimental setup, it was possible to attain a xylans recovery of 71% and a high glucans accessibility of 87% without separating the xylans from the ligno-cellulosic biomass. The xylans recovery was limited by the high temperature of 206° C. of the second pretreatment step, which was needed to reach a pressure of 19 bar. In the case of the third experimental setup, it was possible to operate the second pretreatment step at a low temperature of 196° C., which resulted in a very high xylans recovery of 87% and a high glucans accessibility of 85%, thanks to the important contribution of the entrapped air to the total pressure in the reactor.

The experiments shows that in the second and third experimental setups the temperature and pressure in the reactor are decoupled from steam equilibrium conditions, and it is possible to operate at low temperature, as required to avoid significant xylans degradation, and high pressure, as required to reach a high glucans accessibility, without the complexity and costs of a two-step/two-reactor pretreatment with pre-extraction of hemicellulose in a pressurized vessel.

TABLE 2

Process parameters and results of exemplary process runs of the three experimental setups

|  |  | First experimental set-up (first run) | First experimental set-up (second run) | Second experimental set-up | Third experimental set-up |
|---|---|---|---|---|---|
| First pretreatment step/soaking step | pressure (barg) | 2.8 | 1.8 | 0 | 0 |
|  | temperature (° C.) | 142 | 131 | 94 | 96 |
|  | Time (minutes) | 60 | 60 | 40 | 40 |
|  | Xylans separated (% by mass) | 15% | 3% | 0% | 0% |

TABLE 2-continued

Process parameters and results of exemplary process runs of the three experimental setups

|  |  | First experimental set-up (first run) | First experimental set-up (second run) | Second experimental set-up | Third experimental set-up |
|---|---|---|---|---|---|
| Second pretreatment step/single pretreatment step | pressure (barg) | 13.5 | 18.1 | 19 | 19.9 |
|  | temperature (° C.) | 197 | 210 | 206 | 196 |
|  | Time (minutes) | 4.5 | 7.5 | 7 | 7.5 |
|  | Pressure of pure steam @measured temperature (barg) | 13.6 | 18.1 | 16.6 | 13.3 |
|  | Delta pressure (bar) | 0 | 0 | 2.4 | 6.6 |
| Total pretreatment process | Severity factor | 3.6 | 4.1 | 4.0 | 3.7 |
|  | xylans recovery | 87% | 64% | 71% | 87% |
|  | glucans accessibility | 83% | 88% | 87% | 85% |

The invention claimed is:

1. A process for producing a bio-product from a ligno-cellulosic biomass comprised of a total amount of xylans, a total amount of glucans, a total amount of lignin, and water, wherein the process comprises the steps of:
   a. introducing the ligno-cellulosic biomass, a total amount of gas, and steam into a pressurized reactor of a pressurized reactor assembly operated in a continuous manner at conditions to have a vapor head space in the pressurized reactor, wherein a portion of the steam condenses on the ligno-cellulosic biomass within the pressurized reactor;
   b. maintaining the ligno-cellulosic biomass in the pressurized reactor at a ligno-cellulosic biomass pressure greater than 10 bar for a residence time from 0.5 minutes to 120 minutes, at a vapor head space temperature in a range of 130° C. to 230° C., wherein the ligno-cellulosic biomass pressure is at least 1 bar greater than a pure steam equilibrium pressure at the vapor head space temperature;
   c. refining the ligno-cellulosic biomass by rapidly releasing the ligno-cellulosic biomass pressure while discharging the ligno-cellulosic biomass from the pressurized reactor assembly to create a pre-treated ligno-cellulosic biomass;
   d. hydrolyzing at least a portion of the glucans to an amount of glucose; and
   e. converting at least a portion of the amount of glucose to the bio-product.

2. The process of claim 1, wherein the ligno-cellulosic biomass further comprises an entrapped air, and at least a portion of the gas is entrapped air introduced into the pressurized reactor as part of the ligno-cellulosic biomass.

3. The process of claim 1, wherein the process further comprises a xylans separation step, wherein less than 15% of the total amount of xylans are separated from the ligno-cellulosic biomass prior to introduction into the pressurized reactor.

4. The process of claim 2, wherein the process further comprises a xylans separation step, wherein less than 15% of the total amount of xylans are separated from the ligno-cellulosic biomass prior to introduction into the pressurized reactor.

5. The process of claim 1, wherein the process does not comprise a xylans separation step prior to introduction into the pressurized reactor.

6. The process of claim 2, wherein the process does not comprise a xylans separation step prior to introduction into the pressurized reactor.

7. The process of claim 1, wherein the process further comprises a soaking step, wherein the ligno-cellulosic biomass is soaked in a liquid comprised of water prior to introducing the ligno-cellulosic biomass into the pressurized reactor.

8. The process of claim 2, wherein the process further comprises a soaking step, wherein the ligno-cellulosic biomass is soaked in a liquid comprised of water prior to introducing the ligno-cellulosic biomass into the pressurized reactor.

9. The process of claim 3, wherein the process further comprises a soaking step, wherein the ligno-cellulosic biomass is soaked in a liquid comprised of water prior to introducing the ligno-cellulosic biomass into the pressurized reactor.

10. The process of claim 5, wherein the process further comprises a soaking step, wherein the ligno-cellulosic biomass is soaked in a liquid comprised of water prior to introducing the ligno-cellulosic biomass into the pressurized reactor.

11. The process of claim 7, wherein the process further comprises an aeration step, wherein the ligno-cellulosic biomass is aerated after the soaking step by exposing the ligno-cellulosic biomass to air.

12. The process of claim 8, wherein the process further comprises an aeration step, wherein the ligno-cellulosic biomass is aerated after the soaking step by exposing the ligno-cellulosic biomass to air.

13. The process of claim 9, wherein the process further comprises an aeration step, wherein the ligno-cellulosic biomass is aerated after the soaking step by exposing the ligno-cellulosic biomass to air.

14. The process of claim 10, wherein the process further comprises an aeration step, wherein the ligno-cellulosic biomass is aerated after the soaking step by exposing the ligno-cellulosic biomass to air.

15. The process of claim 1, wherein the ligno-cellulosic biomass is compressed at a compression temperature in a range of 25° C. to less than 100° C. prior to introducing the ligno-cellulosic biomass into the pressurized reactor.

16. The process of claim 1, wherein the pressurized reactor has a pressurized reactor volume and the vapor head space has a vapor head space volume which is between 5% and 80% of the pressurized reactor volume.

17. The process of claim 1, wherein the ligno-cellulosic biomass pressure is selected so that the refining step steam explodes the ligno-cellulosic biomass.

18. The process of claim 1, wherein the vapor head space temperature and the residence time are controlled so that more than 65% of the total amount of xylans are recovered in the pre-treated ligno-cellulosic biomass.

19. The process of claim 1, wherein the ligno-cellulosic biomass pressure is controlled so that the pre-treated ligno-cellulosic biomass comprises an amount of accessible glucans and the amount of accessible glucans in the pre-treated ligno-cellulosic biomass relative to the total amount of glucans in the pre-treated ligno-cellulosic biomass is greater than 80%.

* * * * *